United States Patent [19]
Wang et al.

[11] Patent Number: 5,690,693
[45] Date of Patent: Nov. 25, 1997

[54] TRANSCUTANEOUS ENERGY TRANSMISSION CIRCUIT FOR IMPLANTABLE MEDICAL DEVICE

[75] Inventors: Xintao Wang, Lake Jackson; Mohammed Zafar Amin Munshi, Missouri City, both of Tex.

[73] Assignee: Sulzer Intermedics Inc., Angleton, Tex.

[21] Appl. No.: 482,786

[22] Filed: Jun. 7, 1995

[51] Int. Cl.$^6$ .................................................. A61N 1/378
[52] U.S. Cl. ................................................................ 607/61
[58] Field of Search ............................ 607/33, 61, 32, 607/30, 27; 320/56.14

[56] References Cited

U.S. PATENT DOCUMENTS

| | | |
|---|---|---|
| 3,195,540 | 7/1965 | Waller . |
| 3,454,012 | 7/1969 | Raddi . |
| 3,824,129 | 7/1974 | Fagan . |
| 3,865,101 | 2/1975 | Saper et al. . |
| 3,867,950 | 2/1975 | Fischell . |
| 3,888,260 | 6/1975 | Fischell . |
| 3,942,535 | 3/1976 | Schulman . |
| 4,014,346 | 3/1977 | Brownlee et al. . |
| 4,057,069 | 11/1977 | Dorffer et al. .................. 607/61 |
| 4,082,097 | 4/1978 | Mann et al. . |
| 4,096,856 | 6/1978 | Smith et al. . |
| 4,096,866 | 6/1978 | Fischell . |
| 4,134,408 | 1/1979 | Brownlee et al. . |
| 4,172,459 | 10/1979 | Hepp . |
| 4,275,739 | 6/1981 | Fischell . |
| 4,323,075 | 4/1982 | Langer . |
| 4,409,647 | 10/1983 | Terkanian .................. 363/27 |
| 4,432,363 | 2/1984 | Kakegawa . |
| 4,548,209 | 10/1985 | Wielders et al. . |
| 4,572,191 | 2/1986 | Mirowski et al. ............. 607/61 |
| 4,635,639 | 1/1987 | Hakala et al. . |
| 4,661,107 | 4/1987 | Fink ............................. 623/2 |
| 4,665,896 | 5/1987 | LaForge et al. ............... 128/1 |
| 4,787,389 | 11/1988 | Tarjan . |
| 4,827,936 | 5/1989 | Pless et al. . |
| 4,903,699 | 2/1990 | Baker, Jr. et al. . |
| 5,279,292 | 1/1994 | Baumann et al. ............ 607/137 |
| 5,285,779 | 2/1994 | Cameron et al. .............. 607/5 |
| 5,314,453 | 5/1994 | Jeutter ......................... 607/61 |
| 5,350,413 | 9/1994 | Miller .......................... 607/61 |

FOREIGN PATENT DOCUMENTS

0471421A2  2/1992  European Pat. Off. .

OTHER PUBLICATIONS

Sipex Corporation Signal Processing Excellence; Analog Array ASIC Design Manual, Mar. 1991 (Chapter 3).

*Primary Examiner*—Scott M. Getzow
*Attorney, Agent, or Firm*—Conley, Rose & Tayon, P.C.; Michael F. Heim

[57] ABSTRACT

An improved transcutaneous energy transmission device is disclosed for charging rechargeable batteries in an implanted medical device. A current with a sinusoidal waveform is applied to a resonant circuit comprising a primary coil and a capacitor. Current is induced in a secondary coil attached to the implanted medical device. Two solid state switches are used to generate the sinusoidal waveform by alternately switching on and off input voltage to the resonant circuit. The sinusoidal waveform reduces eddy current effects in the implanted device which detrimentally increases the temperature of the implanted device. The present invention charges the batteries using a charging protocol that reduces charging current as the charge level in the battery increases. The controller preferably is constructed as a pulse width modulation device with a variable duty cycle to control the current level applied to the primary coil. An alignment indicator also is provided to insure proper alignment between the energy transmission device and the implanted medical device.

26 Claims, 5 Drawing Sheets

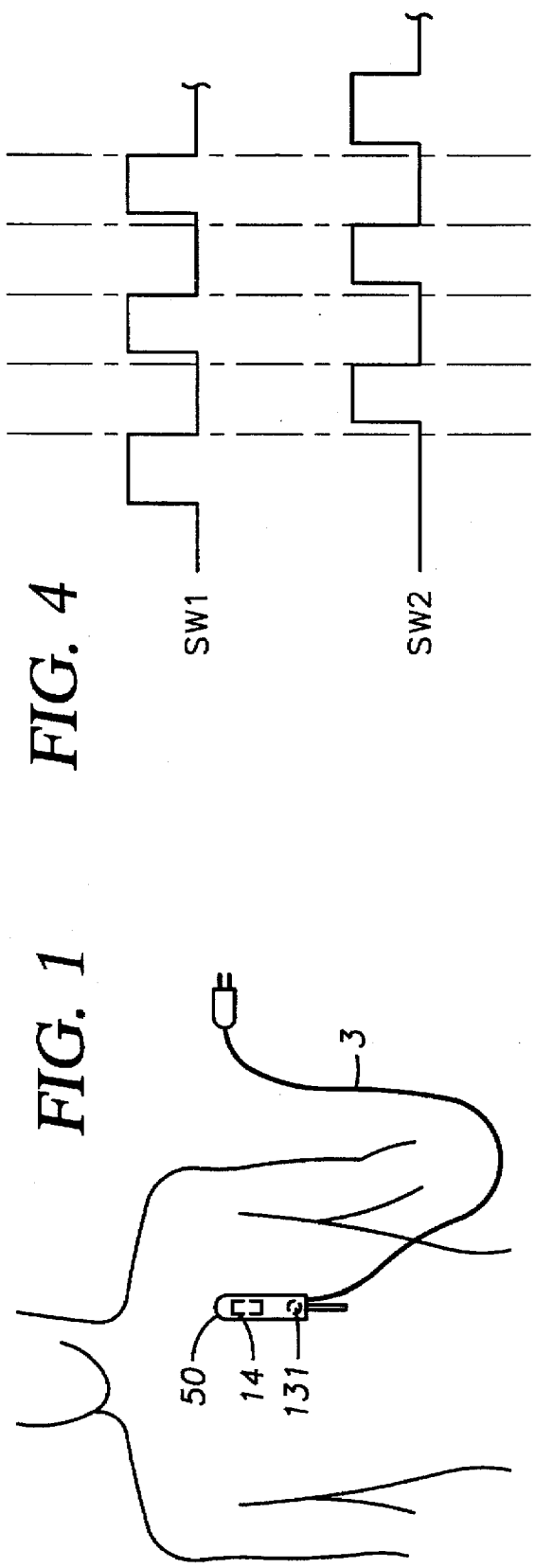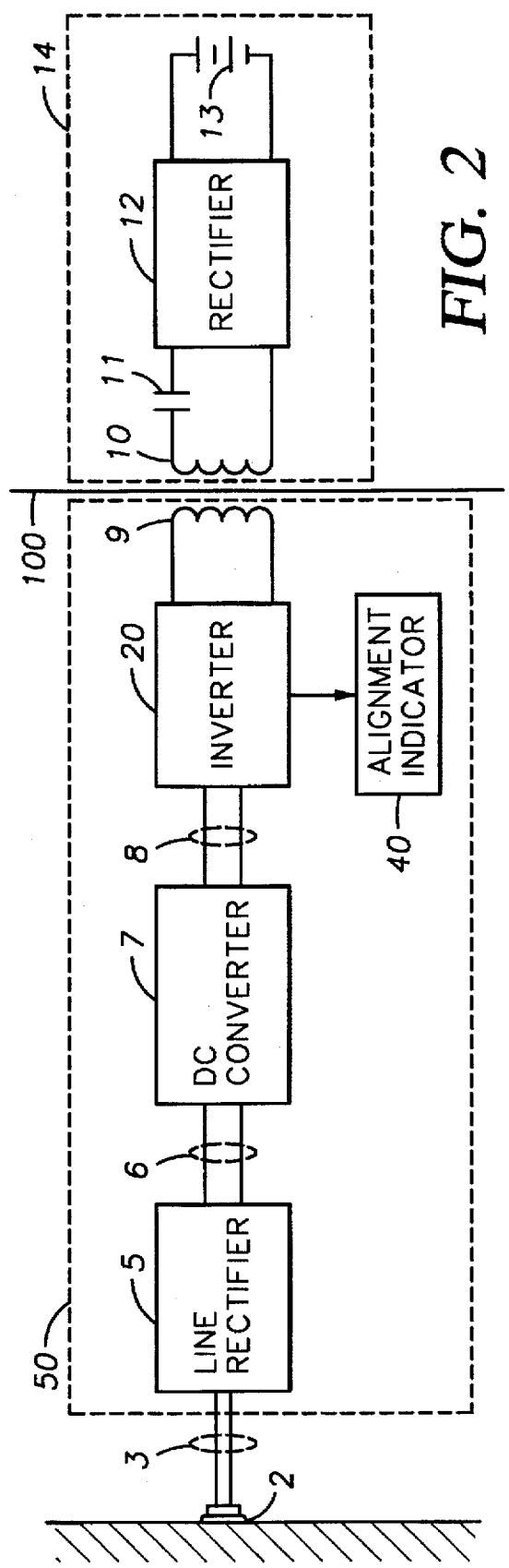

TRANSCUTANEOUS ENERGY TRANSMISSION CIRCUIT FOR IMPLANTABLE MEDICAL DEVICE

BACKGROUND OF THE INVENTION

The present invention relates generally to a power source for an implantable medical device. More particularly, the present invention relates to an external energy transmission device for recharging batteries inside an implantable medical device. Still more particularly, the present invention relates to a charging device for remotely recharging a battery in an implanted medical device. The battery may be of the type disclosed in commonly assigned U.S. Pat. No. 5,411,537, issued May 2, 1995, entitled "Rechargeable Biomedical Battery Powered Devices With Recharging and Control System Therefor."

Currently, battery operable implantable medical devices principally comprise cardiac pacemakers, but they have also been considered for heart assist systems, drug infusion and dispensing systems, defibrillators, nerve and bone growth stimulators, organ stimulators, pain suppressors and implanted sensors, to name a few. The basic cardiac pacemaker device generally comprises an electrode, attached to the heart, that connects by a flexible lead to a pulse generator. The pulse generator includes a microelectronics package which implements the pacemaker functions and a power source for supplying operating power to the microelectronics package and other peripheral devices and components. A fixed rate pacemaker provides continuous pulses to the heart, irrespective of proper beating, while a demand inhibited pacemaker provides pulses only when the heart fails to deliver a natural pulse. Depending upon the various sensed events, the pacemaker stimulates the right atrium, the right ventricle, or both chambers of the heart in succession. The pacemakers in current use incorporate circuits and antennae to communicate noninvasively with external programming transceivers. Most of today's pacemakers are of the demand inhibited type, hermetically sealed, and programmable.

Early pacemakers were powered by disposable primary zinc-mercuric oxide cells. Although the popularity of this system lasted for about 15 years, it suffered from high self-discharge and hydrogen gas evolution. Several mechanisms contributed to battery failure, most of which were related to cell chemistry. In addition, the open-circuit voltage of each cell was only 1.5 V, with several cells connected in series to obtain the required voltage for pacing. Furthermore, because of gas evolution the pacemaker could not be hermetically sealed, and had to be encapsulated in heavy epoxy. In 1970, the average life of the pulse generator was only two years, and 80 percent of explants were necessitated by battery failure.

Because of these limitations, many other power generation and power storage devices have been considered as possible alternates. Research and development efforts focused on primary chemical batteries, nuclear batteries, and rechargeable batteries. Additional development efforts considered separating the stimulator system into two parts, with a power pack located outside the patient's body for transmitting electrical signals through wires to a passive implanted receiver. Cardiac pacemakers based on rechargeable nickel-cadmium and zinc-mercuric systems also were developed. See U.S. Pat. Nos. 3,454,012; 3,824,129; 3,867,950; and 4,014,346. These rechargeable pacemakers incorporated a charging circuit which typically was energized by electromagnetic induction from a device external to the body. The electromagnetic induction produced a current in the pacemaker's charging circuit which was converted to a direct current (DC) voltage for charging the battery. Although this system was incorporated in many cardiac pacemakers, it was unpopular among patients and physicians primarily because frequent recharging was necessary (sometimes on a weekly basis), and the nickel-cadmium system suffered from memory effects which reduced the battery capacity exponentially after each recharge. In addition, the specific energy density of both types of rechargeable batteries was poor, cell voltage was low, the state-of-charge condition was difficult to ascertain, and hydrogen gas liberated during overcharge was not properly scavenged either through a recombination reaction, or hydrogen getters.

Charging nickel-cadmium cells and zinc-mercuric oxide cells are problematic. Both cells have a relatively flat voltage-time curve during the charging process. The flat slope of the voltage versus time curve during charging provides little resolution to ascertain accurately the instantaneous percentage of full charge, and hence nickel-cadmium cells, in particular, provide a poor indication of the state-of-charge condition. Additionally, overcharged nickel-cadmium cells liberate oxygen exothermically at the nickel which migrates to the cadmium electrode and recombines to form cadmium hydroxide. In some situations, particularly during an overcharge condition, the rate of oxygen evolution is higher than the rate of oxygen recombination leading to an excess of gas pressure forcing the cell to vent the excess gas. The overcharge reaction heats the cell which in turn lowers cell voltage. Therefore, a common end-of-charge protocol is to measure cell voltage and determine the point at which the voltage begins to decrease indicating the beginning of the overcharge condition.

Other means of controlling the charging operation have been employed. For example, U.S. Pat. No. 3,775,661 teaches that the pressure build-up internally can be sensed by a diaphragm that is external to the battery. As the pressure within the cell casing increases, the diaphragm is flexed to actuate an associated switch which is located in the battery charging circuit. The closure of the switch deenergizes the charger when the battery internal pressure indicates a fully charged state.

In somewhat similar fashion, U.S. Pat. No. 4,275,739 uses a diaphragm internal to the cell and the deflection of this diaphragm during internal pressure increase indicates the cell reaching full charge. Other examples of systems which control charge operation are U.S. Pat. Nos. 3,824,129; 3,942,535; 3,888,260 and 4,082,097.

Today, most nickel-cadmium chargers control battery charging in a different manner. Common parameters for ascertaining the end-of-charge condition include maximum voltage, maximum time, maximum temperature, a reduction in cell voltage with respect to time, $dV/dt$, $\Delta T$, and $dT/dt$. The details of these end-of-charge indicators can be found in EDN, May 13, 1993.

Both zinc-mercuric oxide and nickel-cadmium cells suffer from additional problems such as memory effect and high self-discharge. Fast recharge often is implemented by charging the battery to some preselected voltage with a relatively high current followed by a smaller trickle charge. It is well known that nickel-cadmium batteries that are fast charged cannot be charged to 100 percent of rated cell capacity. This loss of capacity is called the memory effect. Each time the battery is discharged at some low current rate, and then recharged at a higher current rate, a loss in capacity results. The capacity loss of each recharge cycle accumulates. Cells affected by the memory effect then have to be fully discharged and "reconditioned" before full capacity can be recovered. Because of this loss of capacity and high self-discharge, pacemakers with cells influenced by the memory effect inconveniently were recharged weekly. Rechargeable battery powered pacemakers were designed for a 10 year usable life. Battery chemistry problems, however, reduced the device's usable life to two or three years, the same lifetime as that of disposable primary cells. As a result of the inherent limitations in zinc-mercuric oxide and nickel-cadmium battery cells, the assignee of the present invention has suggested the use of lithium batteries. See U.S. Pat. No. 5,411,537, the teachings of which are incorporated herein.

An additional charging problem arises with respect to the mechanics of recharging an implanted device's rechargeable battery. Due to the increased risk and cost of surgical intervention, it is highly undesirable to operate on a patient in order to access the implanted device to recharge the batteries. Noninvasive methods for recharging implanted batteries are disclosed in the prior art. Some patents disclose a technique for delivering electrical energy through the skin between a transcutaneous energy transfer device and an implanted medical device. For example, U.S. Pat. No. 5,350,413 discloses a transcutaneous energy transfer device comprising a primary coil located on or near the skin and a secondary coil for implantation under the skin. The primary and secondary coils form a transformer so that electrical current in the primary induces current in the secondary coil. An approximation to a half-wave sinusoidal voltage is developed across the primary winding by the action of a field effect transistor (FET) switching a direct current (DC) voltage source across a tuning capacitor. Because, however, of the construction of the energy transmission device, high frequency harmonic components are present in the waveform. These high frequency components induce eddy currents in the implanted device which houses the electronics. The can temperature increases in response to the eddy currents. A rise in temperature of the outer surface of the can may be detrimental to operation of the medical device and surrounding body tissue. To prevent this temperature rise, the prior art charging devices must be operated at very low power levels.

The prior art recharging devices also have a limited depth transmission, requiring the implanted medical device to be located relatively close to the skin. Battery packs for pacemakers are somewhat heavy, and require implantation in muscle tissue, which may be located several inches from the skin. In addition, the prior art devices either contain no mechanism to sense proper alignment between the recharging device and battery, or else have an alignment mechanism which requires the recharging device to be turned off as alignment is measured. Furthermore, existing alignment devices monitor current through the receiving coil (in the implanted device), making it necessary to transmit a signal from the implanted device to the recharging device to determine alignment. Consequently, the energy transmission procedure may be inefficient, causing a longer period to recharge the battery, or else, requiring the recharging operation to be interrupted while alignment is checked. The prior art rechargeable systems also typically require a coil to be positioned externally to the pacemaker, with a relatively large size. This requirement substantially increases the size of the pacemaker package.

It would be desirable, therefore, to provide a battery charging system that overcomes these and other problems associated with rechargeable implantable devices. In particular, it would be desirable to construct a battery charging device which can efficiently charge a battery in an implanted medical device at a relatively high power without excessively heating the device. Similarly, it would be desirable to develop an alignment mechanism that is located in the recharging device, which provides a continuous indication of alignment as the implanted battery is being recharged. It would further be advantageous to develop an energy transmission system that minimizes the size of the receiving coil and permits the coil to be located inside the can. Despite the readily apparent advantages of such a system, to date no such system has been developed.

SUMMARY

The present invention solves the shortcomings and deficiencies of the prior art by constructing a transcutaneous energy transmission device with two solid state switches facilitating the production of a substantially sinusoidal power waveform. The generation of the full sinusoidal wave reduces harmonics and eddy currents which otherwise are generated in the housing (or can) of the implanted device. As a result, heating of the can is minimized. The solid state switches connect a regulated DC voltage across an inductor and capacitor resonant circuit. The inductor forms a primary coil of a transformer in which current is induced in a secondary coil attached to an implanted medical device. The medical device receives the induced current for charging rechargeable batteries.

The present invention can be implemented in a circuit in which a 5 KHz gate signal turns a first MOSFET switch on and off. The gate signal also turns on and off a second MOSFET switch at opposite times than the first MOSFET switch. In addition to minimizing harmonics, the use of the optimum switching frequency reduces the eddy current in the housing (or can) of the implanted device, without causing excessive energy loss.

The present invention must be properly aligned on or near the skin for efficient energy transmission to the implanted medical device. Accordingly, an alignment circuit and indicator are provided to indicate whether the device is properly aligned. The alignment circuit continuously senses current in the primary coil to determine whether the angular and lateral alignment is optimal by sensing a peak alignment, and providing an output signal only when the charging coil is substantially in alignment with the receiving coil in the implanted device.

BRIEF DESCRIPTION OF THE DRAWINGS

Other objects and advantages of the invention will become apparent upon reading the following detailed description and upon reference to the accompanying drawings in which:

FIG. 1 is a drawing showing the charging device placed in the vicinity of the implanted medical device;

FIG. 2 is a schematic block diagram of the charging device in accordance with the preferred embodiment;

FIG. 4 is a timing diagram, depicting the voltage at switches SW1 and SW2 in FIG. 3;

Figure 3:
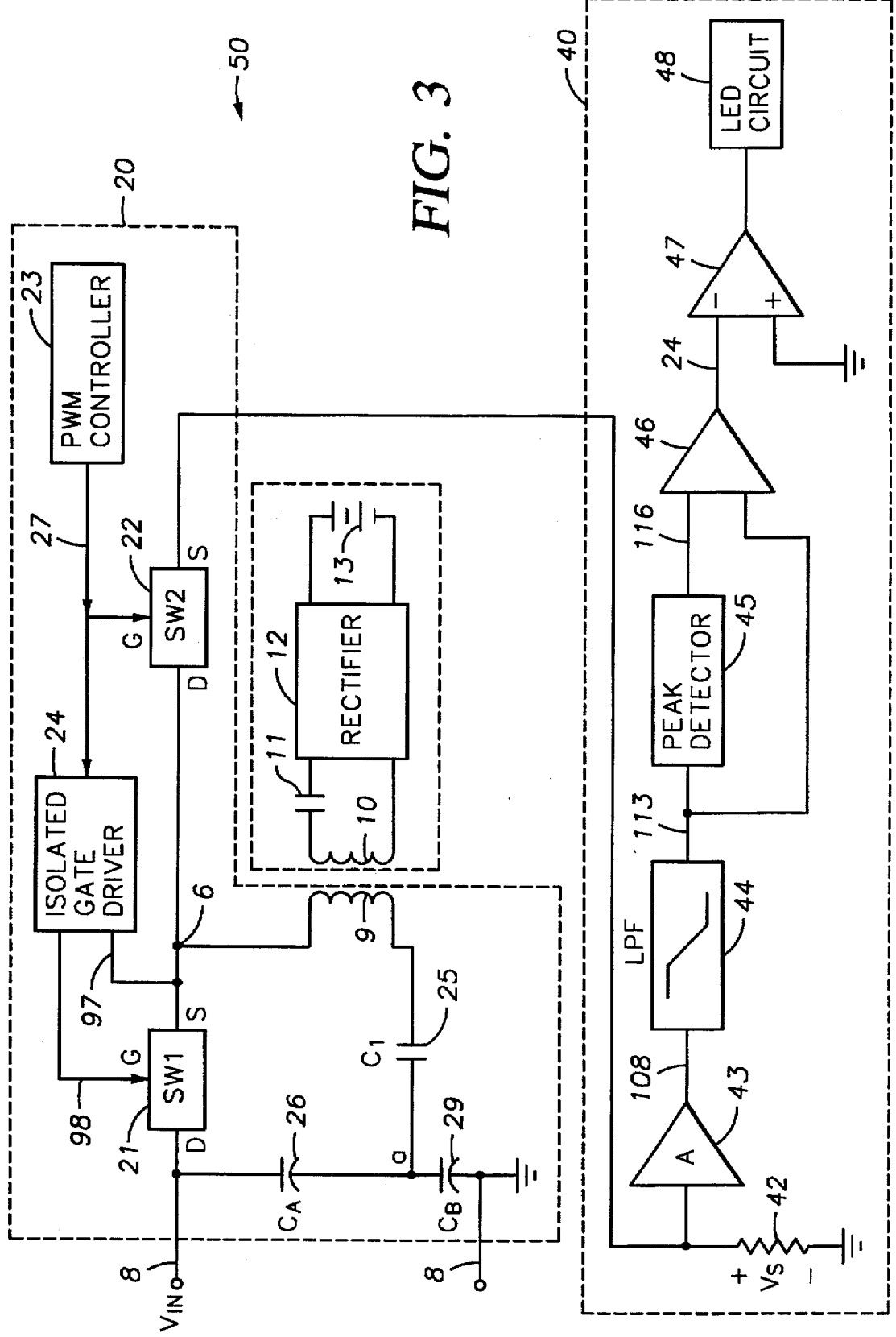
FIG. 3 is a schematic block diagram providing additional details regarding the inverter and alignment indicator shown in FIG. 2.

While the present invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENT

Referring now to FIG. 1, a transcutaneous energy transmission (TET) device 50 is shown operationally charging an implanted medical device 14. In FIG. 1, the medical device 14 is shown implemented in the chest or pectoral region of the patient, as might be the case with a pacemaker device. One skilled in the art will understand, however, that the energy transmission device 50 may be used to charge any implanted medical device, wherever located. In accordance with the preferred embodiment, the implanted medical device 14 is housed in a can made of titanium or stainless steel. The TET device 50 is shown on, or near, the surface of the skin and placed proximally to the implanted device 14. Although the energy transmission device 50 is shown with a generally rectangular configuration it should be understood that the energy transmission device may take any desired shape. Power is provided from an external power source such as a 120 VAC outlet to the TET device 50 via cord 3. An indicator 131 illuminates when TET device 50 is correctly aligned with the implanted device 14 for maximum charging efficiency.

Referring now to FIG. 2, the major subcomponents of TET device 50 generally comprise a line rectifier 5, a DC converter 7 which connects to the line rectifier through conductors 6, and an inverter 20 connecting via conductors 8 to the DC converter 7. An alignment indicator 40 also connects to the inverter 20 to receive signals from inverter 20 when the TET device is properly positioned for maximum efficiency on the patient's skin with respect to the implanted medical device 14.

In the preferred embodiment, an alternating current (AC) voltage is provided by an external power source such as 120 VAC from a wall outlet 2. The 120 VAC source is coupled to the line rectifier through cord 3. The 120 VAC voltage source is converted substantially to a DC voltage by line rectifier 5. One of ordinary skill in the art will recognize that a multitude of known circuit implementations are possible for line rectifier 5 and the present invention shall not be limited to any particular embodiment of line rectifier 5. The unregulated DC voltage generated by the line rectifier 5 is transmitted to the DC converter 7 which regulates the DC voltage and converts the voltage to a DC level appropriate for transcutaneous energy transmission and compatible with the implanted device 14. Various well-known implementations also are possible for DC converter 7, as recognized by one of ordinary skill in the art.

The regulated DC voltage output signal of the DC converter 7 is coupled to the inverter 20 which converts the converter's regulated DC voltage output to a sinusoidal current that flows through a primary coil 9. Electrical current in primary coil 9 electromagnetically induces a corresponding current in a secondary coil 10 which is contained in or adjacent the implanted medical device 14. The electrical energy of primary coil 9 couples transcutaneously between primary and secondary coils through the patient's skin 100.

One of ordinary skill in the art will recognize that other components typically are included in the implanted device 14 beside the secondary coil 10, capacitor 11, rectifier 12, and battery 13 shown in FIG. 2. Other components may include sensors, pulse generators, microprocessors, electrodes, and the like. Capacitor 11 offsets the leakage inductance of the secondary coil 10. The secondary coil 10 and capacitor 11 form a resonant circuit whose natural frequency preferably is designed to be similar to the operational frequency of the TET system to maximize the transcutaneous energy transmission effect.

The rectifier 12 converts the sinusoidal voltage received by the secondary coil 10 and capacitor 11 to a DC voltage for charging battery 13. The rechargeable batteries, suitable for use in the present invention, preferably are based on a number of different lithium chemistries, as disclosed in detail in commonly assigned U.S. Pat. No. 5,411,537, the teachings of which are incorporated hereby by reference. One of ordinary skill in the art, however, will recognize that the present invention may also be used to recharge other types of batteries, as desired.

The present invention focuses on the structure and operation of the inverter 20 and the alignment indicator 40. Accordingly, FIGS. 3–12 show preferred circuit implementations of these components comprising the inverter 20 and the alignment indicator 40. Referring first to FIG. 3, the components comprising the inverter 20 and the alignment indicator 40 are shown in more detail, In accordance with the preferred embodiment, the inverter 20 comprises a PWM (pulse width modulation) controller 23, an isolated gate driver 24, a pair of switches 21, 22, a pair of capacitors $C_A$, $C_B$ and a tuning capacitor $C_1$. The preferred construction of each of these components will be discussed in detail in the following drawings.

Figure 6:
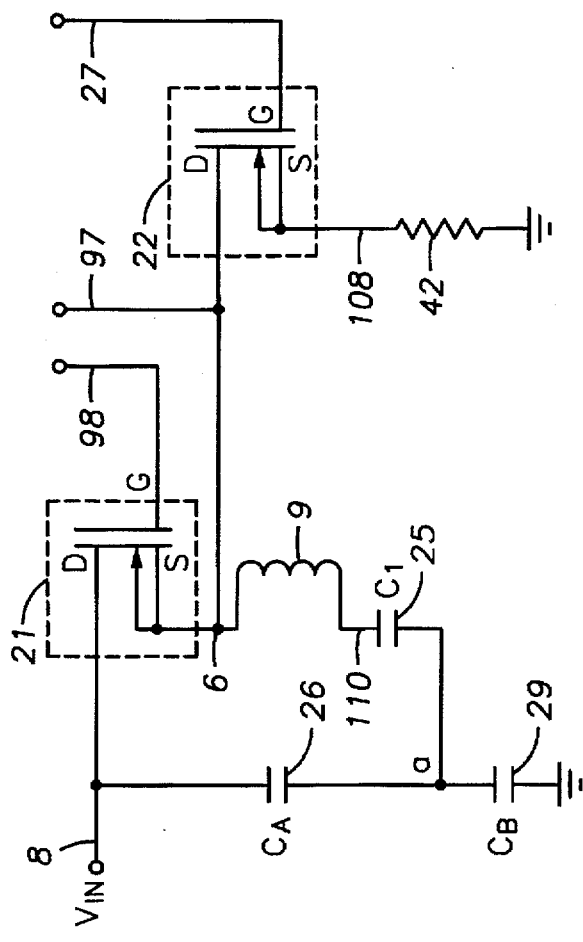
FIG. 6 is an electrical schematic drawing which provides additional detail of the inverter circuit of FIG. 3.

High frequency harmonic content in the current through primary coil 9 will induce eddy currents in the housing or can of the implantable medical device 14 causing a detrimental increase, $\Delta T$, in can temperature. The present invention advantageously minimizes the increase in can temperature $\Delta T$ by generating a charging current signal with a substantially full sinusoidal waveform with little harmonic content. This sinusoidal charging current signal is transcutaneously transmitted to the implanted medical device 14 to charge the associated battery. To generate the desired symmetrical sinusoidal waveform, the inverter 20 uses two switches, 21 and 22. Preferably these switches 21, 22 are solid state devices and, as shown in FIG. 6, may be implemented with metal oxide field effect transistors (MOSFET's). As shown in FIGS. 3 and 4, the output of PWM controller 23 turns switches 21 and 22 on and off alternately with only one switch "on" (i.e., conducting electricity) at any given time. As shown in FIG. 4, a short time period (for example, 2 microseconds) is provided after one switch turns off and before the other switch turns on. This "dead time" between activation of switches 21, 22 (SW 1 and SW2, respectively) insures that the switches are not on simultaneously which may cause a short circuit condition between the voltage input terminal $V_{in}$ and ground. The dead time between switching off one switch and turning on the other also may be modified to control the charging current applied to the batteries, as described more fully below. By increasing the time when both switches 21, 22 are off, the duty cycle of the charging device is decreased, effectively decreasing the power supplied to the primary charging coil 9. Switches 21 and 22 preferably are turned on for the same mount of time each cycle to produce a symmetrical voltage waveform across junctions a and b. The isolated gate driver 24 connects between controller 23 and switch 21 and provides a floating Found to the high side gate signal (the switch 21) to insure the necessary voltage differential between the gate and source of switch 21, while maintaining the driving capacity for high-speed switching. Capacitors 26 and 29, which preferably have identical values, form a voltage divider network and tuning capacitor 25 connects between the common connection point for capacitors 26 and 29 and the negative terminal of transformer 9.

In order to minimize the eddy current induced in the housing or can, the operational frequency of the PWM controller 23 preferably is set at 5 KHz, but can be set between 1 KHz and 40 KHz. Tuning capacitor 25 is selected to generate the desired current amplitude with the primary coil 9 leakage inductance so that a sinusoidal alternating current waveform flows through the primary coil 9 with little high order frequency content. Through proper selection of the value of capacitor 25, the natural resonant frequency of the primary coil 9 and capacitor 25 resonant circuit can be controlled to be below the operational frequency in order to achieve the zero-voltage turn-on of both switches 21 and 22. Furthermore, by varying the value of capacitor 25, the amplitude of the current through primary coil 9 can be modified to provide a wide-range voltage conversion ratio.

In general, the inverter 20 produces a purely sinusoidal transfer current waveform between coils 9 and 10 using a resonant circuit comprising the leakage inductance of primary coil 9 and tuning capacitor 25. Resonance is continuously maintained by alternatively activating switches 21 and 22. The present invention can provide a wide range of charging current from 0 to 1 amperes and charging voltage from 0 to 20 V. The distance between coil 9 and coil 10 may be in the range of 0 to 2.5 inches. Because a pure sinusoidal transfer current waveform is generated, negligible eddy current is induced on the can, thereby maintaining the can temperature relatively constant (and preferably under 40° C.).

Although one of ordinary skill in the art will recognize that many circuit implementations are possible for controller 23, in the preferred embodiment the controller comprises a high speed PWM controller, part number UC3825, manufactured by Unitrode. The PWM controller preferably includes functions such as dual output capabilities, compatibility with voltage or current mode topologies, current limiting, a soft start capability, high source and sink current, and under-voltage lock-out. The PWM controller 23 preferably provides both voltage and current control by modulating the duty cycle of the dual output signal. Thus, referring to FIGS. 3 and 4, PWM controller 23 controls the time when switches 21, 22 (SW1 and SW2, respectively) turn on. By increasing the time period when both switches 21, 22 are off (and thus decreasing the duty cycle), less power is applied to primary coil 9.

Figure 5:
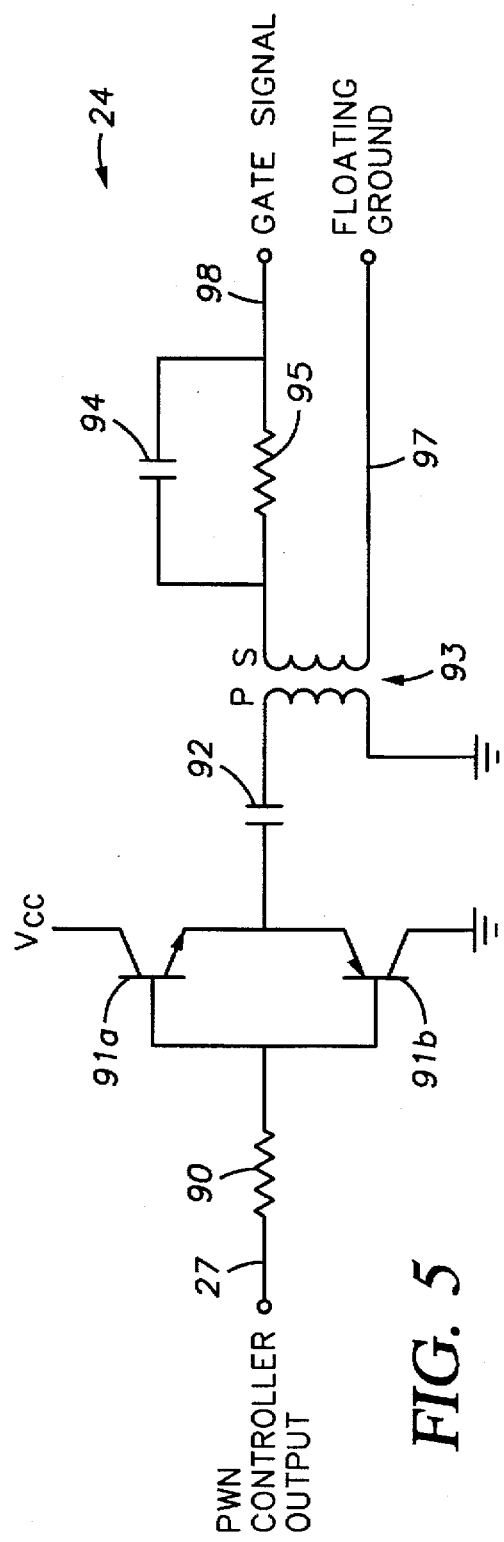
FIG. 5 is an electrical schematic illustration of the isolated gate driver of FIG. 3, constructed in accordance with the preferred embodiment.

Referring now to FIGS. 3 and 5, the preferred construction of the isolated gate driver 24 now will be described. The gate driver 24 preferably comprises an isolation transformer 93, a pair of transistors 91a, 91b, and an RC circuit comprised of capacitor 94 and resistor 95. The output of the PWM controller 23 is provided on conductor 27 as an input to the gate driver 24. The outputs of the gate driver 24 include a gate signal on conductor 98 to the gate terminal G of switch 21, and a floating ground on conductor 97 to the source terminal S of switch 21.

Referring still to FIG. 5, an input resistor 90 connects to conductor 27 and to the base terminals of transistors 91a and 91b. Transistors 91a and 91b form a totem pole output as will be understood by one skilled in the art. A primary coil P of isolation transformer 93 connects to capacitor 92. Capacitor 92 functions to block the DC component of the signal to the primary coil 9 to prevent saturation. The terminals of the secondary coil S of isolation transformer 93 provide an output signal on conductors 97 and 98, respectively. Very fast switching speeds are attained with the capacitive driver formed by capacitor 94 and resistor 95, which comprise an RC network. By having a floating ground on conductor 97, the gate driver 24 is capable of providing a voltage differential between conductors 97 and 98 which will turn on switch 21. In the preferred embodiment, a 7 volt differential is required between the gate and source of switch 21 to turn on switch 21. The isolated gate driver thus provides the necessary voltage differential between the gate and source terminals of switch 21, even though the source of switch 21 does not connect to a fixed ground terminal.

Referring now to FIGS. 3–6, switches 21 and 22 preferably are implemented with MOSFET devices. The secondary coil of isolation transformer 93 (FIG. 5) connects to the gate G and source S terminals of MOSFET switch 21 through conductors 98 and 97 (FIGS. 3 and 6). The source S terminal of MOSFET 21 and the drain D terminal of MOSFET 22 connect to terminal b of primary coil 9. The drain D terminal of MOSFET 21 connects to capacitor 26 and also receives the input regulated DC voltage $V_{in}$ on conductor 8 from DC converter 7. The gate G terminal of MOSFET 22 connects to the other dual output terminal of controller 23 via conductor 27. The source S terminal of MOSFET 22 provides a path for current from the primary coil 9 to ground through the current sensing resistor 42 of the alignment indicator 40. When switch 21 (SW1) turns on, a current path is completed from $V_{in}$, through switch 21, node b, coil 9, capacitor 25, node a, and capacitor 29 to ground. When switch 22 (SW2) turns on, a current path is completed from $V_{in}$, through capacitor 26, node a, capacitor 25, coil 9, node b, switch 22, and resistor 42 to ground.

Referring now to FIG. 3, an additional advantageous feature of the present invention involves an indication of when the TET device 50 is properly positioned for maximum efficiency. When switch 22 is turned on by controller 23, current flows from primary coil 9 through switch 22 and to resistor 42 in alignment indicator 40. Due to the symmetric AC current on the primary coil 9, the current through the switch 22 comprises half of the coil current. Thus, only half of the primary coil current is received by resistor 42. In the preferred embodiment, the DC component of the voltage across the resistor 42 is used as an indication of DC input current from the voltage source $V_{in}$. Alignment indicator 40 provides a light emitting diode (LED) in LED circuit 48 or other output device to indicate proper positioning of the TET device 50 on the patient's skin. A back electromotive force (EMF) effect on the primary coil 9 tends to reduce the DC current from the voltage source $V_{in}$ when the primary coil 9 is not properly aligned with secondary coil 10. The input DC current, therefore, depends on the power draw of the load on the secondary coil (i.e., charging circuitry and battery components 11, 12, and 13 in FIG. 3) and the proximity and orientation of the primary coil 9 to the secondary or receiving coil 10. Therefore, a measurement of the magnitude of the input current preferably is used in the present invention to determine if the TET device 50 is positioned properly for maximum energy transmission efficiency. The following discussion details the construction and operation of the alignment indicator 40 which uses the correlation between the input current and alignment to provide an output signal which indicates when the energy transmission device 50 is sufficiently aligned with the receiving coil 10 in the implanted device 14.

Referring to FIG. 3, the resistance value of resistor 42 preferably is small to minimize the loading effect on the inverter 20 that would otherwise result. In the preferred embodiment, resistor 42 is selected as approximately 0.5 ohms. One of ordinary skill in the art will recognize that the purpose of resistor 42 is to sense current in the primary coil 9 and provide an output signal indicative of the current amplitude and phase shift. Accordingly, although a resistor is preferable, any current sensing device can be used in place of resistor 42.

Referring still to FIG. 3, the alignment indicator 40 preferably includes an amplifier 43, a low pass filter 44 connected to the output of amplifier 43, a peak detector 45 to detect the peak DC current amplitude through switch 22, a difference amplifier 46 to amplify the difference between the peak current amplitude and the present sensed current amplitude, a comparator 47 to compare the amplified difference with ground voltage, and an LED or other output circuit 48. In the preferred embodiment, the LED circuit 48 (or other output device) only provides an output signal indicating alignment if the present sensed current amplitude is within a predetermined range of the peak value.

Current flow through resistor 42 from switch 22 generates a voltage $V_s$ across resistor 42 which is amplified by amplifier 43 and filtered by low-pass filter 44 to effectively obtain the DC component of the waveform through resistor 42, and to filter out the AC portion of the waveform. The peak detector 45 senses the peak amplitude value of the output signal on conductor 113, which connects to the output terminal of the low-pass filter 44. The peak detector 45 stores the peak value, unless a higher amplitude is subsequently sensed. If a higher value is subsequently sensed, the peak detector 45 replaces the stored peak value with the new peak value. The output signal of the peak detector 45 on conductor 116 corresponds to the peak positive voltage sensed by the peak detector 45. This peak voltage (which is scaled to provide a threshold value that is somewhat less than the peak value), is provided as an input to the difference amplifier 46. The other input to the difference amplifier comprises the current sensed output of the low pass filter (conductor 113). The difference amplifier 46 amplifies the difference between the scaled peak value, and the present sensed value, and provides an output signal to comparator 47. Comparator 47 compares the difference with ground voltage, and turns on the LED circuit 48 when the current sensed value is greater than the scaled peak value. This condition will occur when the TET device 50 is positioned properly over the implanted device. If the lateral placement of the TET device is misaligned with respect to the receiving coil, or if the TET device 50 is positioned at a nonoptimal angle with respect to the implanted device for peak transmission efficiency, the scaled peak value will be greater than the present output voltage at the output terminals of filter 44, and the comparator 47 will produce an output signal de-activating the LED circuit 48.

One of ordinary skill in the art will recognize that a plurality of circuit implementations are possible for the amplifier 43, low-pass filter 44, peak detector 45, difference amplifier, comparator 47 and LED circuit 48 of alignment indicator 40. In addition, the functions of two or more of these components may be performed by a single device. The circuit schematics of FIGS. 7-12 are shown as the preferred embodiment of the present invention.

Figure 7:
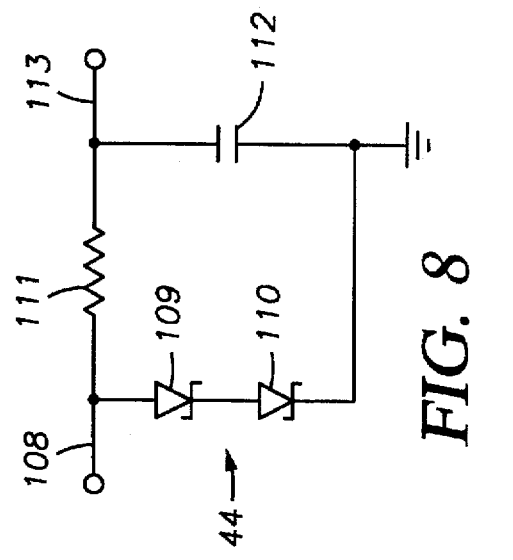
FIG. 7 is an electrical schematic drawing of the amplifier of FIG. 3 with a low pass filter, in accordance with the preferred embodiment.

As noted above, the voltage waveform across resistor 42 includes both AC and DC components. In the preferred embodiment, the AC component is filtered to permit examination of the DC component. Referring now to FIGS. 3 and 7, amplifier 43 is configured as an inverting amplifier, with an operational amplifier 103, an input resistor 102, a feedback resistor 105, a feedback capacitor 106, and an output resistor 107. The negative ratio of the resistance of feedback resistor 105 to the resistance of resistor 102 determines the voltage gain of the amplifier 43. Preferably, the gain is set at 100. Therefore, the resistance of resistor 105 should be one hundred times greater than that of resistor 102. Resistance values of 44.9 Kohms for resistor 105 and 449 ohms for resistor 102 are preferred, but numerous other values are possible as will be understood by one skilled in the art. Capacitor 106, together with resistor 102, provide low-pass filter capabilities to amplifier 43. A resistor 104 connects the positive input terminal of operational amplifier 103 to ground. The output terminal of operational amplifier 103 connects to feedback resistor 105, capacitor 106, and output resistor 107. The output of amplifier 43 (which preferably indicates a negative voltage value) is provided on conductor 108 to low pass filter 44.

Figure 8:
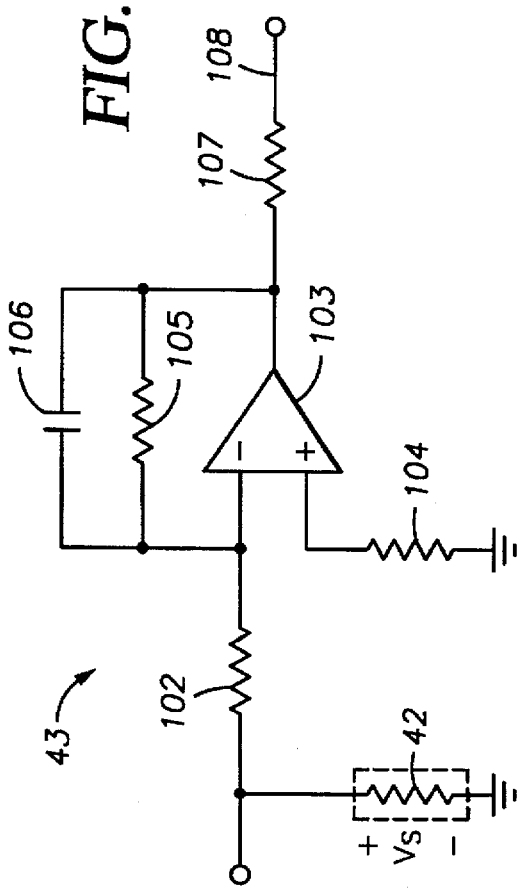
FIG. 8 is an electrical schematic illustration of the low pass filter of FIG. 3, constructed in accordance with the preferred embodiment.

Referring now to FIGS. 3 and 8, the low pass filter 44 preferably comprises a pair of series connected zener diodes 109, 110, resistor 111 and capacitor 112. Zener diodes 109 and 110, arranged in series, function to clamp the output of amplifier 43 to the combined clamping voltage of zener diodes 109, 110. Resistor 111 and capacitor 112 form an RC filter, which sets the corner frequency of low pass filter 44.

Figure 9:
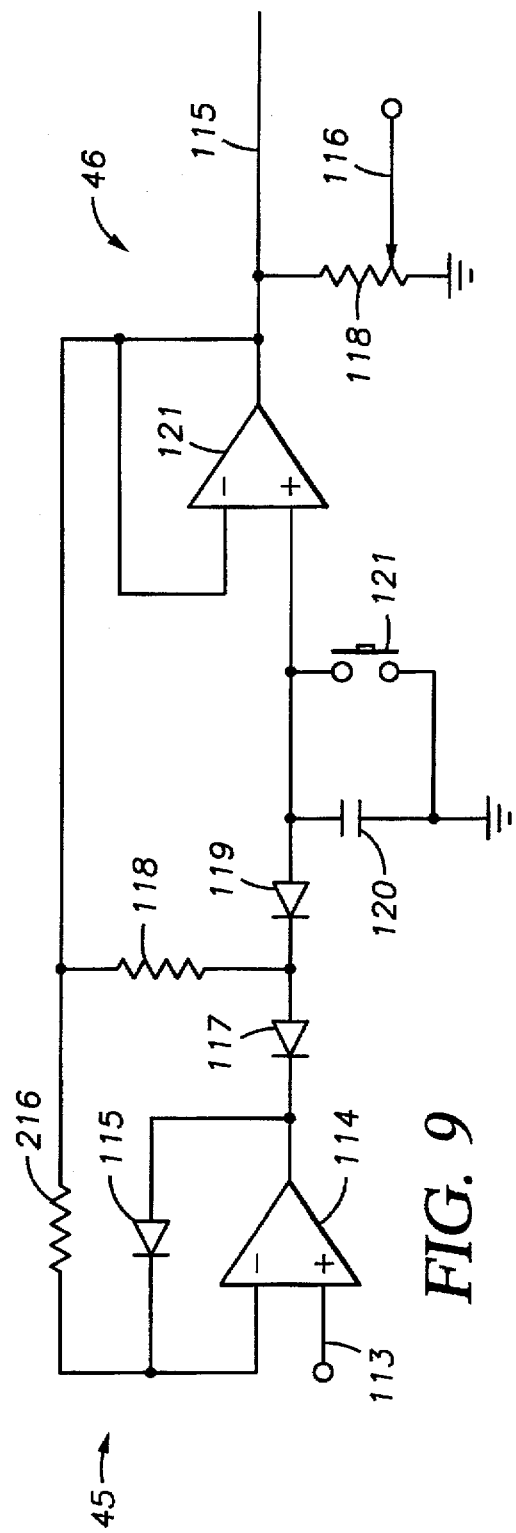
FIG. 9 is an electrical schematic drawing depicting the preferred embodiment of the peak detector of FIG. 3.

Referring now to FIGS. 3 and 9, the preferred construction and operation of the peak detector 45 will now be described. In the preferred embodiment, peak detector 45 comprises an operational amplifier 114, peak storage capacitor 120, and voltage follower 46. The low-pass filtered output signal from filter 44 connects through conductor 113 to the positive input terminal of operational amplifier 114. The output terminal of operational amplifier 114 connects to the cathode of diode 117, the anode of which connects to the cathode of diode 119. Current from operational amplifier 114 (with a negative amplitude) flows through diodes 117 and 119, charging storage capacitor 120 to a voltage indicative of the peak value at the negative input of operational amplifier 114. Diode 115 prevents operational amplifier 114 from saturating in the absence of peak values, and resistor 216 provides a path through which the current from diode 115 can flow. Switch 121 resets the peak detector output signal to 0 V upon closure of that switch.

When a new peak arrives at the negative input of operational amplifier 114, the output of op amp 114 swings in the negative direction, turning diode 115 off (preventing current flow through resistor 216) and turning diodes 117 and 119 on, permitting capacitor 120 to charge. As the input voltage on conductor 113 drops, the output of operational amplifier 114 swings in the positive direction, turning off diode 117 and diode 119. As a result, capacitor 120 maintains its peak voltage charge, with diode 119 and resistor 118 limiting the leakage of capacitor 120. As the output voltage continues in the positive direction, diode 115 turns on to prevent saturation of the op amp 114.

The voltage follower buffer 46 not only provides a high input impedance to minimize loading on other stages of the circuitry, but also scales down the peak detected voltage through the use of a manually adjustable potentiometer 118. Potentiometer 118 connects between the output of operational amplifier 121 and ground to provide an adjustable voltage divider in which conductor 116 carries the scaled down peak voltage to an input of comparator 47. The output of operational amplifier 121 is fed back to the inverting input of amplifier 121 and is provided via conductor 115 to peak detector 45.

Figure 10:
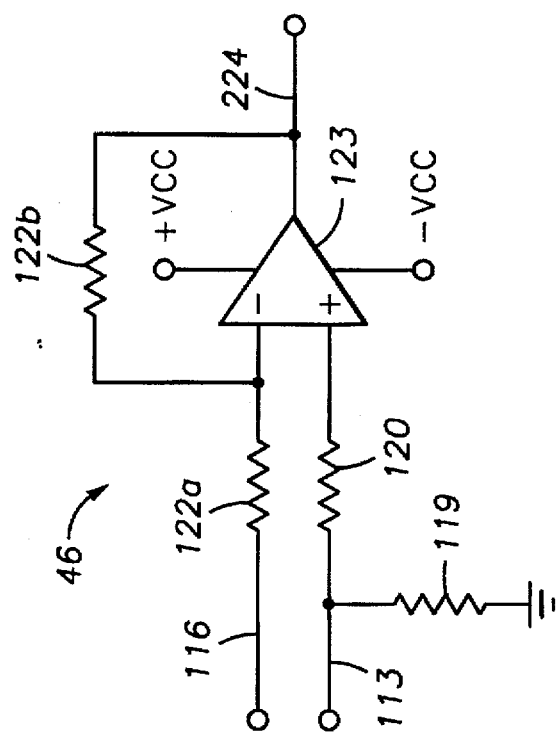
FIG. 10 is an electrical schematic of the difference amplifier of FIG. 3 and the associated circuitry.

Referring now to FIG. 10, the difference amplifier 46 preferably comprises an operational amplifier 123, a feedback resistor 122b, and input resistors 120, 122a. The output signal from peak detector 45 couples to the negative input terminal of operational amplifier 123 through resistor 122a. The output signal from the low-pass filter 44 couples through resistor 120 to the positive input terminal of operational amplifier 123 operational amplifier 123 amplifies the difference between the scaled peak value on conductor 116, and the present sensed value on conductor 113, and provides the amplified difference as its output 224. In the preferred embodiment of FIG. 10, the resistance of resistor 122b is equal to the resistance of resistor 119, and the resistance of resistor 122a is equal to the resistance of resistor 120, to provide a gain for difference amplifier 46 that equals the ratio of resistor 122b to resistor 122a.

Figure 11:
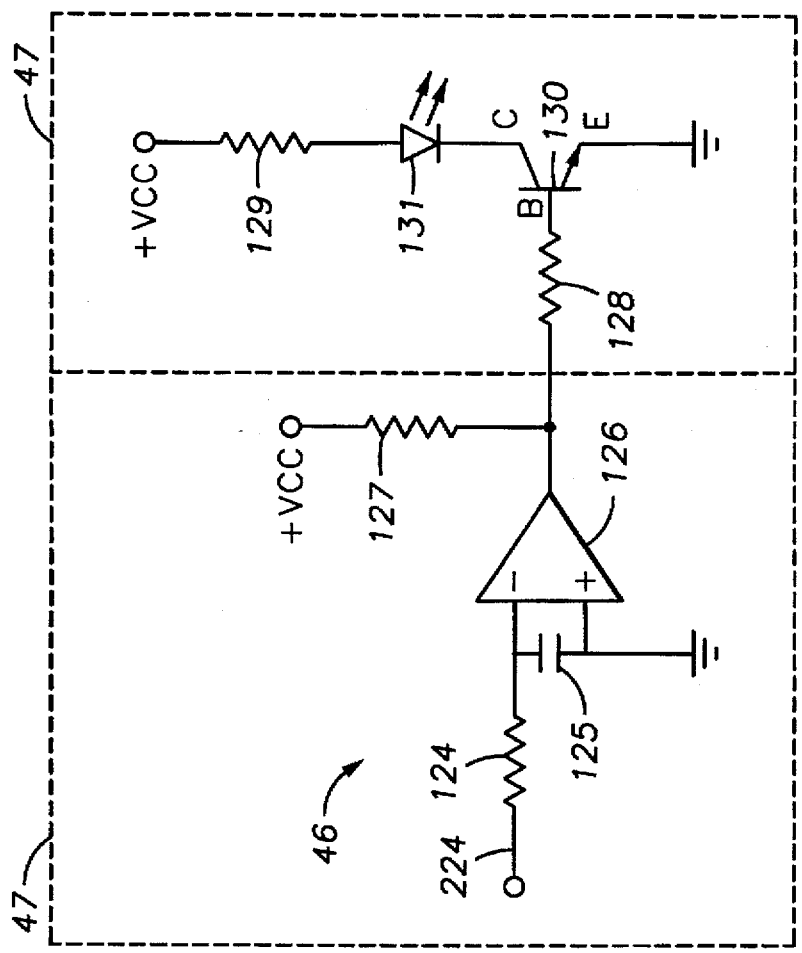
FIG. 11 is an electrical schematic drawing of the comparator and LED circuit of FIG. 3.

Referring now to FIGS. 3 and 11, the comparator 47 and LED circuit 48 are shown in detail. The comparator circuit 47 preferably comprises an operational amplifier 126, a pull-up resistor 127, input resistor 124, and capacitor 125. The LED circuit 48 includes an LED 131, transistor 130, current limiting resistors 128 and 129. The output of difference amplifier 46 preferably connects via conductor 224 to the negative terminal of operational amplifier 126, through input resistor 124. The positive input terminal of op amp 126 connects to ground, and to the negative input terminal of op amp 126 through capacitor 125. The output of op amp 126 provides an input to the LED circuit 48 to turn on LED 131, or an alternative output device. Resistor 127 comprises a pull-up resistor which may be necessary if operational amplifier 126 has an open-collector output stage. In the preferred embodiment, the output terminal of operational amplifier 126 connects to the base terminal B of transistor 130 through current limiting resistor 128. Power from the voltage source $+V_{cc}$ is provided to LED 131 through resistor 129 when transistor 130 is turned on by the supply of sufficient base current from the operational amplifier 126 to the base terminal B of the transistor 130. Although an NPN transistor is shown in FIG. 11, one of ordinary skill in the art will recognize that other types of LED driver circuits are possible, including the use of PNP transistors, and the present invention should not be construed as limited by the particular circuit embodiment shown in FIG. 11. Similarly, although an LED 131 is shown as the output device, one skilled in the art will also understand that other output devices, such as audible indications, may be used as an alternative, or in addition to LED 131.

To efficiently charge the batteries in the implanted medical device 14 and avoid many of the problems discussed herein, the TET device 50 employs a current-step charging protocol. The preferred charge current protocol is discussed in detail in commonly assigned U.S. Pat. No. 5,411,537, the teachings of which have been incorporated herein.

While a preferred embodiment of the present invention has been described, one skilled in the art will understand that many modifications can be made to the present invention without departing from its principles. The following claims should not be construed as limited to the preferred embodiment, but instead should be construed broadly to cover all modifications and equivalents, which will be apparent to one skilled in the art.

What is claimed is:

1. A transcutaneous energy transmission device for transmitting electrical power to an implanted medical device with a rechargeable battery to recharge the battery, said transcutaneous energy transmission device comprising:
   a primary coil for transmitting said power transcutaneously to said medical implanted device;
   a capacitor coupled to said primary coil, said primary coil and said capacitor forming a resonant circuit;
   an alignment indicator electrically coupled to said primary coil to indicate proper alignment between said transcutaneous energy transmission device and said implanted medical device, said alignment indicator indicating proper alignment based on current through said primary coil;
   a controller for controlling the power provided to said resonant circuit; and
   a first switch and a second switch coupled to said controller, and being alternatively switched on and off by said controller to produce a sinusoidal current waveform through said primary coil.

2. The device of claim 1 wherein said first switch and said second switch comprise solid state devices.

3. The device of claim 2 wherein solid state switches comprise field effect transistors.

4. The device of claim 1 wherein said controller operates between 1 KHz and 40 KHz.

5. The device of claim 4 wherein said controller operates between 1 KHz and 10 KHz.

6. The device of claim 5 wherein said controller operates substantially at 5 KHz.

7. The device of claim 1, wherein said sinusoidal current waveform eliminates eddy current losses in said implanted medical device.

8. A transcutaneous energy transmission device for transmitting electrical power to an implanted medical device with a rechargeable battery to recharge the battery, said transcutaneous energy transmission device comprising:
   a primary coil for transmitting said power transcutaneously to said medical implanted device;
   a capacitor coupled to said primary coil, said primary coil and said capacitor forming a resonant circuit;
   a controller for controlling the power provided to said resonant circuit;
   a first switch and a second switch coupled to said controller, and being alternatively switched on and off by said controller to produce a sinusoidal current waveform through said primary coil; and
   an alignment indicator to indicate proper alignment between said transcutaneous energy transmission device and said implanted medical device, wherein said alignment indicator comprises a sensor for sensing DC current waveform amplitude through at least one of said first or second switches.

9. The device of claim 8 wherein said alignment indicator further comprises a peak detector for detecting and storing the peak DC amplitude value of said current flowing through at least one of said first or second switches.

10. A transcutaneous energy transmission device for transmitting electrical energy to an implanted medical device for providing power to said implanted medical device to charge battery cells in said implanted medical device, said transcutaneous energy transfer device comprising:
   a primary coil for transmitting said power transcutaneously to said medical implanted device;
   a capacitor coupled to said primary coil, said primary coil and said capacitor forming a resonant circuit;
   a controller for controlling the power provided to said resonant circuit; and
   an alignment indicator circuit electrically coupled to said primary coil to indicate proper alignment between said transcutaneous energy transmission device and said implanted medical device, wherein said alignment indicator circuit senses current flow through said primary coil to determine alignment.

11. The device of claim 10 wherein said transcutaneous energy transmission device further comprises a plurality of solid state switches for providing current to said primary coil and to said capacitor to produce a current signal with a sinusoidal waveform.

12. The device as in claim 11, wherein the controller comprises a PWM controller.

13. The device as in claim 12, wherein the alignment indicator circuit senses the amplitude of the current signal through at least one of said plurality of solid state switches to determine proper alignment.

14. A transcutaneous energy transmission device for transmitting electrical power to an implanted medical device that includes a receiving coil for charging battery cells associated with said implanted medical device according to a charging protocol, said transcutaneous energy transmission device comprising:
   a line rectifier for converting alternating current (AC) voltage to substantially direct current (DC) voltage;
   a DC converter for conditioning and regulating said DC voltage to provide a DC current input;
   an inverter receiving the DC current input and producing a relatively high current signal with a substantially sinusoidal waveform to a primary coil, said primary coil transmitting a charging current transcutaneously to said medical implanted device;
   wherein said inverter includes:
      a capacitor coupled to said primary coil, said primary coil and said capacitor forming a resonant circuit; and
      a PWM controller that produces a gate signal for said resonant circuit; and
   wherein said transcutaneous energy transmission device further comprises an alignment indicator circuit which senses the DC current input to said inverter to determine proper alignment between said transcutaneous energy device and said implanted medical device.

15. The device of claim 14, wherein said charging protocol comprises a series of steps and wherein the charging current in a first step is greater than the charging current in a subsequent step.

16. The device of claim 14 wherein said transcutaneous energy transmission device further comprises a plurality of solid state switches for providing the current signal to said primary coil and said capacitor and which produce the current signal with a substantially sinusoidal waveform.

17. The device of claim 14 wherein said alignment indicator indicates proper lateral and angular alignment of said transcutaneous energy transmission device with said implanted medical device.

18. The device in claim 14, wherein said transcutaneous energy transmission device is capable of recharging batteries located in said implanted medical device when the distance between said primary coil and said receiving coil is less than or equal to approximately 2.5".

19. The device of claim 14 wherein said PWM controller operates between 1 KHz and 40 KHz.

20. The device of claim 19 wherein said PWM controller operates between 1 KHz and 10 KHz.

21. The device of claim 20 wherein said PWM controller operates substantially at 5 KHz.

22. The device of claim 14, wherein said battery cells are located in a can.

23. The device of claim 22, wherein said power signal with a substantially sinusoidal waveform minimizes eddy current in said can.

24. The device of claim 22, wherein said power signal with a substantially sinusoidal waveform minimizes harmonics in said can.

25. The device of claim 22, wherein said power signal with a substantially sinusoidal waveform minimizes temperature increases in said can.

26. The device of claim 14, wherein said PWM controller is capable of varying the power transmitted by said energy transmission device.

* * * * *